United States Patent [19]

Ross

[11] Patent Number: 4,663,017
[45] Date of Patent: May 5, 1987

[54] COMBUSTIBLES SENSOR

[75] Inventor: David F. Ross, Euclid, Ohio

[73] Assignee: The Babcock & Wilcox Company, New Orleans, La.

[21] Appl. No.: 754,668

[22] Filed: Jul. 11, 1985

Related U.S. Application Data

[63] Continuation of Ser. No. 564,955, Dec. 23, 1983, abandoned, which is a continuation-in-part of Ser. No. 239,864, Mar. 2, 1981, abandoned.

[51] Int. Cl.[4] .............................................. G01N 27/46
[52] U.S. Cl. ..................................... 204/409; 204/424; 204/427
[58] Field of Search ........................ 204/1 S, 421–429, 204/409

[56] References Cited

U.S. PATENT DOCUMENTS

| | | | |
|---|---|---|---|
| B 843,038 | 2/1976 | Sandler | 204/1 S |
| 3,869,370 | 3/1975 | Sayles | 204/1 S |
| 3,960,500 | 6/1976 | Ross et al. | 204/1 S |
| 4,154,664 | 5/1979 | Renevot | 204/428 |
| 4,240,890 | 12/1980 | Watanabe et al. | 204/428 |
| 4,430,192 | 2/1984 | Maeda | 204/428 |

OTHER PUBLICATIONS

*Webster's New Collegiate Dictionary,* 1960, p. 945.

*Primary Examiner*—T. Tung
*Attorney, Agent, or Firm*—Vytas R. Matas; Robert J. Edwards

[57] ABSTRACT

A modified zirconia oxygen sensor is disclosed wherein gas flows through inner (14) and outer tubes (12) and wherein one electrode (18) is attached to the inner surface of the inner tube (14), and the second electrode (16) is attached to the outer surface of the inner tube (14). The outer catalytic surface of inner tube (14) is made inert so that an oxygen potential difference is produced between the electrodes (16, 18) which results in a voltage output, as read by the oxygen analyzer (42), which is proportional to the initial level of the combustible in the gas. The utilization of inner (14) and outer tubes (12) wherein the portion of the gas sample contacting the active electrode (18) is maintained separate from the portion of the gas sample contacting the inactive electrode (16) prevents back or edge diffusion between the electrodes.

4 Claims, 2 Drawing Figures

COMBUSTIBLES SENSOR

CROSS-REFERENCE TO RELATED APPLICATIONS

This is a continuation of application Ser. No. 564,955, filed Dec. 23, 1983, now abandoned, which was a continuation-in-part of application Ser. No. 239,864, filed Mar. 2, 1981, now abandoned.

TECHNICAL FIELD

The present invention relates to a device for determining the presence of various combustibles within a mixture, and more particularly to a device for determining the presence of carbon monoxide and other combustibles within a combustible mixture that contains oxygen.

BACKGROUND ART

Prior art devices for determining the presence of carbon monoxide and other combustibles utilize techniques such as infrared adsorption, chemiluminescence, surface adsorption cells and the like. While such methods are capable of determining the required levels of carbon monoxide and other combustibles, they tend to be expensive, can be susceptible to long term drift, and can be difficult to calibrate.

One known type of combustibles sensor, as shown in U.S. Pat. No. 4,005,001, supplies a gaseous mixture of oxygen and fuel to first and second electrodes on opposite surfaces of an oxygen ion conductive solid electrolyte cell in the form of a disk having electrodes on opposite surfaces thereof, wherein the electrodes are composed of different materials each exhibiting a different catalytic action on the gaseous mixture at a given temperature. The difference in oxygen potentials established at the respective electrodes as a result of the dissimilar catalytic action produces oxygen ion conductivity in the solid electrolyte cell which produces an electrical signal having a magnitude which is indicative of the combustible present in the mixture. It has been found that with this disk type of electrolyte, concentration gradients with very low flow rates will force diffusion of the reacted and unreacted gas to opposite electrode surfaces which can cause confusing results.

Because of the foregoing, it has now become desirable to develop a combustibles sensor having improved flow sensitivity and reproducibility.

SUMMARY OF THE INVENTION

The present invention solves the aforementioned problems associated with the prior art as well as other problems by providing a combustibles sensor which has improved flow sensitivity and reproducibility. More specifically, the present invention provides a modified zirconia oxygen sensor wherein gas flows through inner and outer tubes, and wherein one electrode is on the inner surface of the inner tube and the second electrode is on the outer surface of the inner tube. The velocity of the exit gases is increased with respect to that of the entrance gases by means of an orifice or other flow restrictor at the tube outlets. The outer catalytic surface is made inert by means of a cement or other material which poisons its catalytic activity. Because of the tubular configuration, sample gas flow in split, so that gas flow exists on both sides of the inner tube, and there is no mixing of the reacted and unreacted gas.

When no combustibles are present, the sensor output is near zero because there is equal oxygen concentration on both sides of the sensor. When operating at sufficient temperature to produce catalytic activity between the combustible gas and oxygen on the inside of the sensor, there is a resulting decrease of oxygen in the inner sample because oxygen is consumed in the reaction. For example, where CO is the combustible to be detected:

$$CO + \tfrac{1}{2}O_2 \rightarrow CO_2$$

The $O_2$ differential between the inner and outer surface of the inner tube will produce a voltage proportional to the initial level of CO in the gas mixture. In the tubular construction of the present invention, once the reaction occurs at the active inner electrode, the gas is physically constrained to remain separated from the outer surface of the inner tube. Accordingly, back diffusion or edge diffusion is essentially eliminated.

DESCRIPTION OF THE PREFERRED EMBODIMENT

Figure 1:
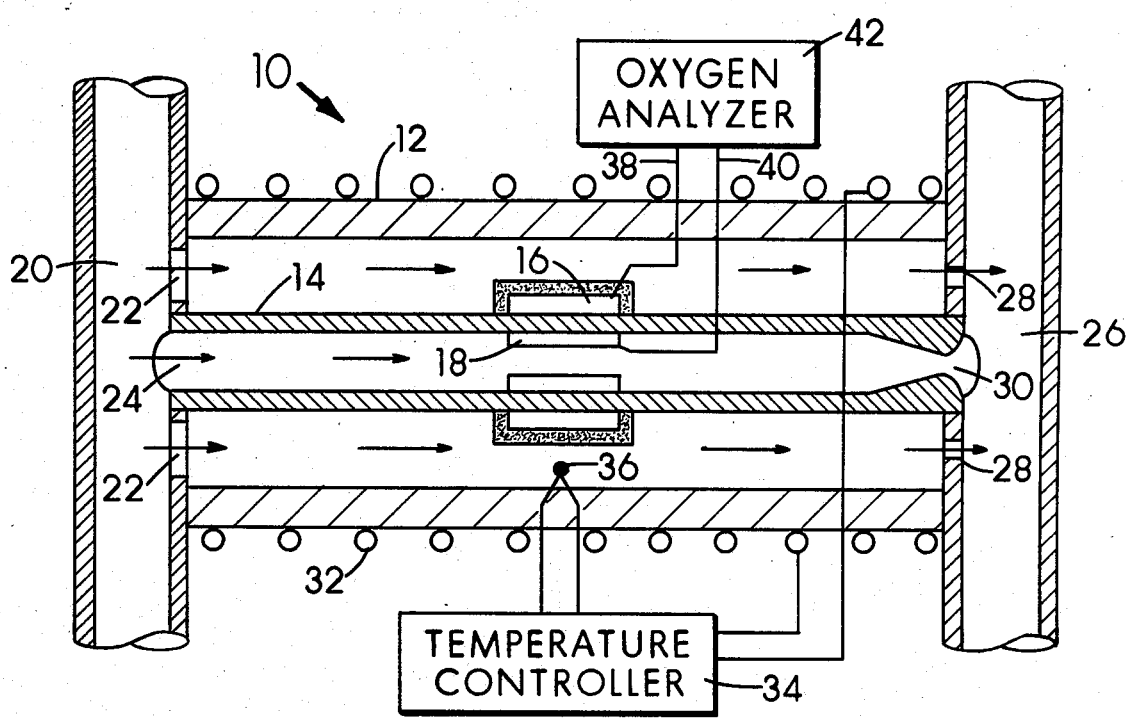
FIG. 1 is a schematic representation of the apparatus of the present invention.

Referring now to the drawings where the illustrations are for the purpose of describing the preferred embodiment and are not intended to limit the invention hereto, FIG. 1 is a schematic representation of the apparatus of the present invention and illustrates a combustibles sensor assembly 10 comprising an outer tube 12, an oxygen ion conductive solid electrolyte cell in the form of an inner tube 14, a first annular electrode 16 adhered to the outer diameter of the inner tube 14, and a second annular electrode 18 adhered to the inner diameter of the inner tube 14. In accordance with the preferred embodiment of the present invention, the electrodes 16 and 18 can be electrically connected to a zirconia oxygen analyzer of the type shown in U.S. Pat. No. 3,960,500.

The outer tube 12 receives a sample of gas from a furnace stack 20 through a plurality of holes 22 formed in the side of the stack, while the inner tube 14 receives the sample through a central opening 24 formed in the stack, the gas sample then flowing through the tubes and being exhausted to an exhaust plenum 26 via orifices 28 and 30 exiting to the plenum (26). The orifice 30 is formed integrally with the tube 14 to provide an orifice having an outlet area which is approximately 25% of the inlet area of the inlet 24. The exit orifices 28 are approximately 25% of the inlet orifice 22 area. By forming the outlet 30 as a venturi, the exit flow is made to be approximately 16 times that of the inlet velocity which assures elimination of any back diffusion because of the high velocity outlet.

The inner tube 14 is formed of a zirconia material, and the outer surfaces thereof is made inert by coating it with a cement or other material which posions its catalytic activity. The electrodes 16 and 18 can be formed from platinum or some other noble metal.

A heating coil 32 surrounds the outer tube 12 and is operatively connected to a temperature controller 34 which effectively regulates the temperature of the sensor assembly 10 to a desired operating temperature, typically between 400° C. and 1000° C., as monitored by a thermocouple unit 36. Electrical leads 38 and 40 connect the electrodes 16 and 18 to the oxygen analyzer 42.

By making the outer electrode 16 inert, the oxygen analyzer 42, as shown in U.S. Pat. No. 3,960,500 previously noted, is converted into a combustibles sensor. Using the measurement of CO as an example, the $O_2$ differential between the inner and outer surfaces of the tube 14 produces a voltage output, as recorded by the oxygen analyzer 42, which is proportional to the initial level of CO in the gas mixture.

By using the configuration illustrated, wherein the gas sample is split and flows both inside and outside the zirconia cell defined by the inner tube 14 and exits at a velocity greater than the velocity at which it entered, the gas which contacts the active inner electrode 18 is always maintained separate from the gas which contacts the inactive outer electrode 16, so that the back or edge diffusion present in prior art devices is essentially eliminated.

Figure 2:
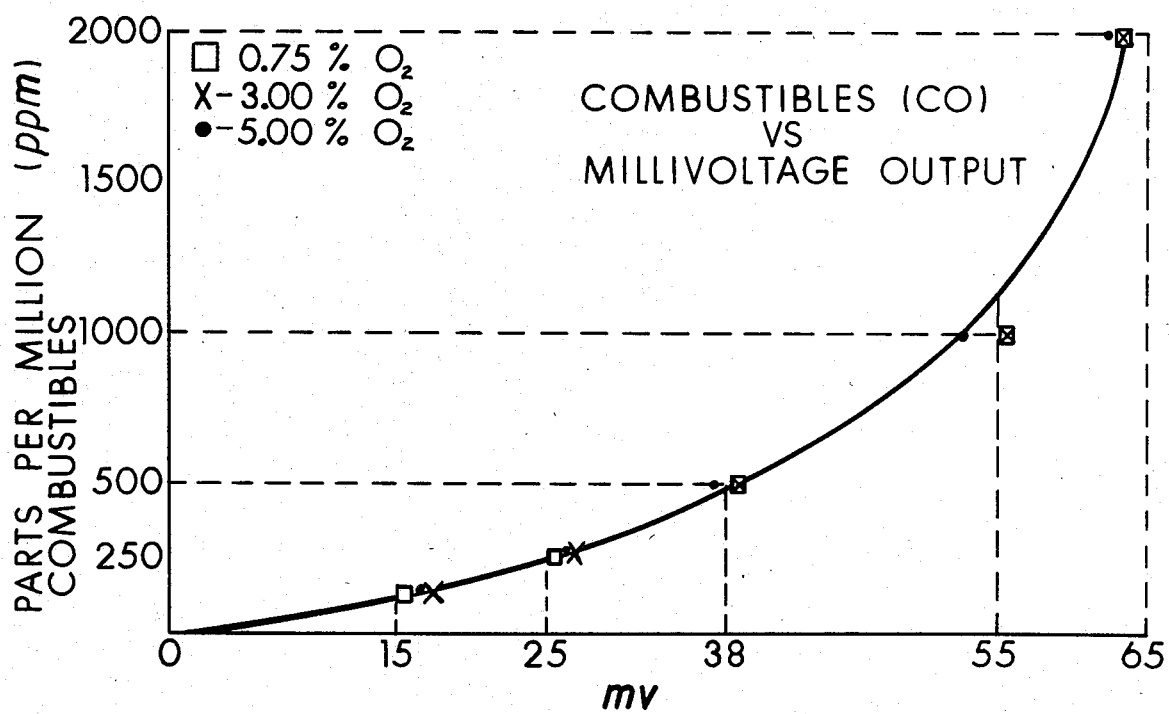
FIG. 2 is a graphical representation of sensor voltage output for various concentrations of oxygen in a carbon monoxide and oxygen mixture.

An example of the use of the zirconia oxygen analyzer as part of the combustibles sensor of the invention is illustrated by FIG. 2, in which the voltage output as determined by the oxygen analyzer 42 is plotted versus the parts per million of CO in actual gas mixtures with various oxygen concentration. While FIG. 2 illustrates the sensing of carbon monoxide, it can be appreciated that the system can also be calibrated to sense other combustibles in fuel mixtures containing oxygen.

Certain modifications and improvements will occur to those skilled in the art upon reading the foregoing. It should be understood that all such modifications and improvements have been deleted herein for the sake of conciseness and readability but are properly within the scope of the following claims.

We claim:

1. An apparatus for determining the presence of predetermined combustible constituents in an excess oxygen gas mixture, comprising:

an oxygen ion conductive solid electrolyte cell including a first solid electrolyte tube, having an inlet end and an outlet end and an inside and an outside surface; a first electrode, attached to the outside surface of said first tube and a second electrode, attached to the inside surface of said first tube;

means for conducting a sample of said gas mixture simultaneously to said first and said second electrodes along separate paths having no gas diffusion between said paths, said means including a second tube, having an inlet end and an outlet end, surrounding said first tube such that a first portion of said gas mixture flows in the space defined between said first and said second tubes and in contact with said first electrode, and a second portion of said gas mixture flows through said first tube only and in contact with said second electrode, said first electrode supporting a first rate of catalytic combustion reactivity between said oxygen and said combustible constituents of said gas mixture, and said second electrode supporting a second rate of catalytic combustion reactivity between said oxygen and said combustible constituents of said gas mixture, said first rate being different from said second rate such that an oxygen potential difference between said first and said second electrodes is produced, said solid electrolyte cell developing an output signal corresponding to said oxygen potential difference which is indicative of the combustible constituents present in said gas mixture;

a venturi, formed integrally with the outlet end of said first tube and located downstream of said second electrode, said venturi having an outlet cross-sectional flow area less than ¼ that of the inlet cross-sectional flow area of said inlet end of said first tube, for increasing the velocity of said second portion of said gas mixture exiting from said first tube over the velocity of said second portion of said gas mixture entering said first tube to minimize the diffusion of said second portion of said gas mixture back into the outlet end of said first tube; and velocity increasing means, located at the outlet end of said second tube and downstream of said first electrode, for increasing the velocity of said first portion of said gas mixture exiting from the space defined between said first and said second tubes over the velocity of said first portion of said gas mixture entering said defined space to minimize the diffusion of said first portion of said gas mixture back into the outlet end of said second tube.

2. The apparatus as defined in claim 1 wherein said first tube is formed of a zirconia material, and said first and second electrodes are formed of platinum.

3. The apparatus as defined in claim 1 further including heating means surrounding said second tube, and temperature control means operatively connected to said heating means for maintaining the temperature of said gas mixture in contact with said electrodes at a substantially constant predetermined temperature.

4. The apparatus as defined in claim 1 further including a first plurality of orifices having a total inlet cross-sectional flow entrance area located at the inlet end of said second tube for admitting said first portion of said gas mixture to said defined space between said first and said second tubes, and wherein said velocity increasing means comprises a second plurality of orifices of sufficient cross-sectional flow area to form a total outlet cross-sectional flow exit area from said defined space of less than ¼ of the total inlet cross-sectional flow entrance area of said first plurality of orifices.

* * * * *